United States Patent
Tonomura et al.

(10) Patent No.: US 7,053,233 B2
(45) Date of Patent: May 30, 2006

(54) SILANE COMPOUND HAVING AT LEAST TWO PROTECTED FUNCTIONAL GROUPS AND METHOD FOR PREPARING THE SAME

(75) Inventors: Yoichi Tonomura, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/104,588

(22) Filed: Apr. 13, 2005

(65) Prior Publication Data

US 2005/0234254 A1  Oct. 20, 2005

(30) Foreign Application Priority Data

Apr. 14, 2004  (JP) ............................. 2004-119293

(51) Int. Cl.
 *C07F 7/04* (2006.01)
(52) U.S. Cl. ...................... 556/413; 556/424; 556/443; 556/444; 556/445; 556/446
(58) Field of Classification Search ................ 556/413, 556/424, 443, 444, 445, 446
See application file for complete search history.

(56) References Cited

U.S. PATENT DOCUMENTS

2004/0254301 A1  12/2004  Tsukimawashi et al.

FOREIGN PATENT DOCUMENTS

| EP | 0 537 744 A1 | 4/1993 |
|---|---|---|
| JP | 3414134 B2 | 4/2003 |
| JP | 2004-18795 A | 1/2004 |

OTHER PUBLICATIONS

Tezuka et al, "Synthesis and Surface Formation of Three-Component Copolymers Having Polystyrene-block-poly(dimethylsiloxane) Graft Segements", pp. 8251-8258, 1995.*

Y. Tezuka et al., "Synthesis of polyurethane-polystyrene graft copolymer using uniform-size polystyrene with a diol end-group," Polymer, vol. 34, No. 24, 1993, pp. 5180-5185.
Chemical Abstract of JP 62 195389 A2, Aug. 28, 1987.

* cited by examiner

*Primary Examiner*—Samuel Barts
(74) *Attorney, Agent, or Firm*—Birch, Stewart, Kolasch & Birch, LLP (57) ABSTRACT

A silane compound of the following formula (1) having two or more protected functional groups $$A\text{-}R\text{—}Si(CH_3)_nX_{3-n} \qquad (1)$$

wherein A represents a group of the following formula

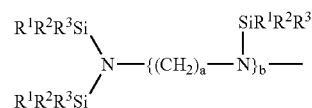

wherein $R^1$, $R^2$ and $R^3$ each independently represent a monovalent hydrocarbon group having 1 to 10 carbon atoms, a is an integer of 1 to 10, and b is an integer of 1 to 10, or

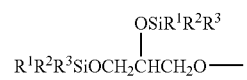

wherein $R^1$, $R^2$ and $R^3$ are as defined above, R represents a linear or branched, divalent hydrocarbon group having 2 to 10 carbon atoms, X represents a halogen atom or an organoxy group having 1 to 10 carbon atoms, and n is 0, 1 or 2 is prevented from the reaction of the functional groups per self when undergoing modification or treatment. When the protection is removed after introduction of the protected functional groups, quantitative and efficient introduction of the two or more functional groups is ensured, resulting in more developed effects of modification and addition.

15 Claims, 8 Drawing Sheets

SILANE COMPOUND HAVING AT LEAST TWO PROTECTED FUNCTIONAL GROUPS AND METHOD FOR PREPARING THE SAME

CROSS-REFERENCE TO RELATED APPLICATION

This non-provisional application claims priority under 35 U.S.C. §119(a) on Patent Application No. 2004-119293 filed in Japan on Apr. 14, 2004, the entire contents of which are hereby incorporated by reference.

This invention relates to a protected, functional group-bearing silane compound which is useful as a modifier for polymers, a coating additive, an adhesive, a silane coupling agent, a surface treating agent or the like, and also a method for preparing the silane compound.

BACKGROUND OF THE INVENTION

Silane compounds having protected functional groups are useful as a modifier for polymers, a coating additive, an adhesive, a silane coupling agent, a surface treating agent or the like.

For instance, Japanese Patent No. 3,414,134 describes an N,N-(bistrimethylsilyl)aminopropylsilane compound whose amino group is protected with trimethylsilyl groups and which is useful as a modifier for amino-modified silicone oils.

JP-A 2004-18795 describes a compound having a protected primary amino group and an alkoxysilyl group, i.e. an N,N-(bistrimethylsilyl)aminopropylsilane compound. This compound is used to introduce the amino group into a living polymer terminal group of styrene-butadiene obtained by the anionic polymerization. The amino group-bearing styrene-butadiene rubber prepared using this compound as an anionic polymerization terminal modifier is useful as a base polymer for tire formulated with silica, carbon black or the like.

Such a silane compound having protected functional groups is also useful as an additive for coatings or adhesives. For example, when a silane compound having a protected amino group is added to an epoxy resin composition, a stable composition is obtained as not showing any reactivity in a moisture-free or blocked system. On contact with moisture, de-protecting through hydrolysis takes place, thereby providing a one-component curable composition of the type wherein the amino group is regenerated to cause curing to be initiated.

In this way, on use for modification of anionic polymerization terminal or addition to the coatings or adhesives, the silane compound having protected functional group is able to prevent the reaction of the protected functional group. If the protected group is subsequently de-protected, the functional group can be regenerated and introduced in a quantitative and efficient manner. However, these compounds enable only one functional group per molecule to be introduced. This may leads to a reduced degree of development of the effect attained by the introduction of the functional group. Hence, there is a demand for a modifier or an additive ensuring that the effect of the introduction of functional groups is more likely to develop.

SUMMARY OF THE INVENTION

Accordingly, it is an object of the invention to provide a silane compound which is able to introduce two or more functional groups on use for modification and allows its effect of modification and addition to be developed more significantly.

It is another object of the invention to provide a method for preparing a silane compound of the type mentioned above.

In order to achieve the above object, we have made intensive studies. As a result, it has been found that a silane compound of the following general formula (1) having two or more protected functional groups and obtained by addition reaction of a compound of the following general formula (2) or (3) with a hydrogen silane compound of the following general formula (4) is able to prevent the reaction of a functional group upon modification or addition thereof. Moreover, after introducing the protected functional groups, the removal of the protection leads to quantitative and efficient introduction of two or more functional groups, thus enabling the effects of modification and addition to be more conspicuously developed. The invention has been accomplished based on the above finding.

More particularly, the invention provides a silane compound of the following formula (1) having two or more protected functional groups wherein A represents a group of the following formula wherein $R^1$, $R^2$ and $R^3$ each independently represent a monovalent hydrocarbon group having 1 to 10 carbon atoms, a is an integer of 1 to 10, and b is an integer of 1 to 10, or a group of the following formula wherein $R^1$, $R^2$ and $R^3$ are as defined above, R represents a linear or branched, divalent hydrocarbon group having 2 to 10 carbon atoms, X represents a halogen atom or an organoxy group having 1 to 10 carbon atoms, and n is 0, 1 or 2.

The invention also provides a method for preparing the silane compound as defined above which comprises reacting in the presence of a platinum catalyst a compound of the following general formula (2) or (3) having a double bond wherein A is as defined above, and R' represents a linear or branched divalent hydrocarbon group having 1 to 8 carbon atoms, and a hydrogen silane compound of the following general formula (4)

wherein X and n are as defined above.

According to the invention, a silane compound having two or more protected functional groups is prevented from a reaction of the functional groups per self when undergoing modification or treatment. When the protection is removed after introduction of the protected functional groups, quantitative and efficient introduction of the two or more functional groups is ensured, resulting in more developed effects of modification and addition.

DETAILED DESCRIPTION OF THE PREFERRED EMBODIMENTS

The compound of the invention consists of a silane compound having two or more protected functional groups and represented by the following general formula (I)

wherein A represents a group of the following formula wherein $R^1$, $R^2$ and $R^3$ each independently represent a monovalent hydrocarbon group having 1 to 10 carbon atoms, a is an integer of 1 to 10, and b is an integer of 1 to 10, or a group of the following formula wherein $R^1$, $R^2$ and $R^3$ are as defined above, R represents a linear or branched, divalent hydrocarbon group having 2 to 10 carbon atoms, X represents a halogen atom or an organoxy group having 1 to 10 carbon atoms, and n is 0, 1 or 2.

$R^1$, $R^2$ and $R^3$ each independently represent a monovalent hydrocarbon group having 1 to 10 carbon atoms, preferably 1 to 6 carbon atoms and include a linear, branched or cyclic alkyl group, alkenyl group, aryl group or the like. Specific examples include a methyl group, an ethyl group, a propyl group, an isopropyl group, a butyl group, an isobutyl group, a tert-butyl group, a pentyl group, a cyclopentyl group, a hexyl group, a cyclohexyl group, a heptyl group, an octyl group, a decyl group, a vinyl group, an allyl group, a propenyl group, a phenyl group and the like. R represents a linear or branched, divalent group having 2 to 10 carbon atoms, preferably 3 to 10 carbon atoms and include an alkylene group, an aralkylene group and the like. Specific examples include a trimethylene group, a tetramethyl group, a hexamethylene group, an isobutylene group and the like. X represents a halogen atom such as chlorine, fluorine, bromine, and iodine, or an organoxy group having 1 to 10 carbon atoms, preferably 1 to 6 carbon atoms and includes an alkoxy group such as a methoxy group, an ethoxy group, a propoxy group, an n-butoxy group, an isobutoxy group, a tert-butoxy group or the like, an acyloxy group such as an acetoxy group or the like, an acryloxy group, a methacryloxy group, a phenoxy group, or the like.

Specific examples of the silane compound having two or more protected functional groups include N,N',N'-tris(trimethylsilyl)-N-(2-aminoethyl)-3-aminopropyltrimethoxysilane, N,N',N'-tris(trimethylsilyl)-N-(2-aminoethyl)-3-aminopropylmethyldimethoxysilane, N,N',N'-tris(trimethylsilyl)-N-(2-aminoethyl)-3-aminopropyldimethylmethoxysilane, N,N',N'-tris(trimethylsilyl)-N-(2-aminoethyl)-3-aminopropyltriethoxysilane, N,N',N'-tris(trimethylsilyl)-N-(2-aminoethyl)-3-aminopropylmethyldiethoxysilane, N,N',N'-tris(trimethylsilyl)-N-(2-aminoethyl)-3-aminopropyldimethylethoxysilane, N,N',N'-tris(trimethylsilyl)-N-(2-aminoethyl)-3-aminopropyltrichlorosilane, N,N',N'-tris(trimethylsilyl)-N-(2-aminoethyl)-3-aminopropylmethyldichlorosilane, N,N',N'-tris(trimethylsilyl)-N-(2-aminoethyl)-3-aminopropyldimethylchlorosilane, N,N',N'-tris(trimethylsilyl)-N-(6-aminohexyl)-3-aminopropyltrimethoxysilane, N,N',N'-tris(trimethylsilyl)-N-(6-aminohexyl)-3-aminopropylmethyldimethoxysilane, N,N',N'-tris(trimethylsilyl)-N-(6-aminohexyl)-3-aminopropyldimethylmethoxysilane, N,N',N'-tris(trimethylsilyl)-N-(6-aminohexyl)-3-aminopropyltriethoxysilane, N,N',N'-tris(trimethylsilyl)-N-(6-aminohexyl)-3-aminopropylmethyldiethoxysilane, N,N',N'-tris(trimethylsilyl)-N-(6-aminohexyl)-3-aminopropyldimethylethoxysilane, N,N',N'-tris(trimethylsilyl)-N-(6-aminohexyl)-3-aminopropyltrichlorosilane, N,N',N'-tris(trimethylsilyl)-N-(6-aminohexyl)-3-aminopropylmethyldichlorosilane, N,N',N'-tris(trimethylsilyl)-N-(6-aminohexyl)-3-aminopropyldimethylchlorosilane, 6,7-bis(trimethylsiloxy)-4-oxaheptyltrimethoxysilane, 6,7-bis(trimethylsiloxy)-4-oxaheptylmethyldimethoxysilane, 6,7-bis(trimethylsiloxy)-4-oxaheptyldimethylmethoxysilane, 6,7-bis(trimethylsiloxy)-4-oxaheptyltriethoxysilane, 6,7-bis(trimethylsiloxy)-4-oxaheptylmethyldiethoxysilane, 6,7-bis(trimethylsiloxy)-4-oxaheptyldimethylethoxysilane, 6,7-bis(trimethylsiloxy)-4-oxaheptyltrichlorosilane, 6,7-bis(trimethylsiloxy)-4-oxaheptylmethyldichlorosilane, 6,7-bis(trimethylsiloxy)-4-oxaheptyldimethylchlorosilane, 6,7-bis(triethylsiloxy)-4-oxaheptyltrimethoxysilane, 6,7-bis(triethylsiloxy)-4-oxaheptylmethyldimethoxysilane, 6,7-bis(triethylsiloxy)-4-oxaheptyldimethylmethoxysilane, 6,7-bis(triethylsiloxy)-4-oxaheptyltriethoxysilane, 6,7-bis(triethylsiloxy)-4-oxaheptylmethyldiethoxysilane, 6,7-bis(triethylsiloxy)-4-oxaheptyldimethylethoxysilane, 6,7-bis(triethylsiloxy)-4-oxaheptyltrichlorosilane, 6,7-bis(triethylsiloxy)-4-oxaheptylmethyldichlorosilane, 6,7-bis(triethylsiloxy)-4-oxaheptyldimethylchlorosilane, 6,7-bis(tert-butyldimethylsiloxy)-4-oxaheptyltrimethoxysilane, 6,7-bis(tert-butyldimethylsiloxy)-4-oxaheptylmethyldimethoxysilane, 6,7-bis(tert-butyldimethylsiloxy)-4-oxaheptyldimethylmethoxysilane, 6,7-bis(tert-butyldimethylsiloxy)-4-oxaheptyltriethoxysilane, 6,7-bis(tert-butyldimethylsiloxy)-4-oxaheptylmethyldiethoxysilane, 6,7-bis(tert-butyldimethylsiloxy)-4-oxaheptyldimethylethoxysilane, 6,7-bis(tert-butyldimethylsiloxy)-4-oxaheptyltrichlorosilane, 6,7-bis(tert-butyldimethylsiloxy)-4-oxaheptylmethyldichlorosilane, 6,7-bis(tert-butyldimethylsiloxy)-4-oxaheptyldimethylchlorosilane, 6,7-bis(triisopropylsiloxy)-4-oxaheptyltrimethoxysilane, 6,7-bis(triisopropylsiloxy)-4-oxaheptylmethyldimethoxysilane, 6,7-bis(triisopropylsiloxy)-4-oxaheptyldimethylmethoxysilane, 6,7-bis(triisopropylsiloxy)-4-oxaheptyltriethoxysilane, 6,7-bis(triisopropylsiloxy)-4-oxaheptylmethyldiethoxysilane, 6,7-bis(triisopropylsiloxy)-4-oxaheptyldimethylethoxysilane, 6,7-bis(triisopropylsiloxy)-4-oxaheptyltrichlorosilane, 6,7-bis(triisopropylsiloxy)-4-oxaheptylmethyldichlorosilane, and 6,7-bis(triisopropylsiloxy)-4-oxaheptyldimethylchlorosilane.

The silane compound of the general formula (1) having two or more protected functional groups is prepared, for example, by reacting, in the presence of a platinum catalyst, a compound of the following general formula (2) or (3) having a double bond $$A\text{-}R'\text{-}CH=CH_2 \quad (2)$$

$$A\text{-}CH=CH_2 \quad (3)$$

wherein A is as defined hereinbefore, and R' represents a linear or branched divalent hydrocarbon group having 1 to 8 carbon atoms, and a hydrogen silane compound of the following general formula (4)

$$HSi(CH_3)_nX_{3-n} \quad (4)$$

wherein X and n are as defined hereinbefore.

In the above formula, R' is a linear or branched divalent hydrocarbon group having 1 to 8 carbon atoms and includes an alkylene group such as a methylene group, an ethylene group, a trimethylene group, a tetramethylene group or the like, an arylene group such as a phenylene group or the like, an aralkylene group or the like.

Specific examples of the compound of the general formula (2) include N,N',N'-tris(trimethylsilyl)-N-allylethylenediamine, N,N',N'-tris(trimethylsilyl)-N-allylhexamethylenediamine, glycerinebis(trimethylsilyl)monoalllyl ether, glycerinebis(triethylsilyl)monoallyl ether, glycerinebis(tert-butyldimethylsilyl)monoallyl ether, glycerinebis(triisopropylsilyl)monoallyl ether, and the like.

Specific examples of the compound of the above general formula (3) include N,N',N'-tris(trimethylsilyl)-N-vinylethylenediamine, N,N',N'-tris(trimethylsilyl)-N-vinylhexamethylenediamine, glycerinebis(trimethylsilyl)monovinyl ether, glycerinebis(triethylsilyl)monovinyl ether, glycerinebis(tert-butyldimethylsilyl)monovinyl ether, glycerinebis(triisopropylsilyl)monovinyl ether and the like.

Specific examples of the hydrogen silane compound of the general formula (4) used for the above reaction include trimethoxysilane, methyldimethoxysilane, dimethylmethoxysilane, triethoxysilane, methyldiethoxysilane, dimethylethoxysilane, trichlorosilane, methyldichlorosilane, dimethylchlorosilane and the like.

The mixing ration between the double bond-bearing compound of formula (2) or (3) and the hydrogen silane compound of formula (4) is not critical. From the standpoint of reactivity and productivity, the mixing ratio is preferably within a range of 0.5 to 2 moles, more preferably from 0.8 to 1.2 moles of the hydrogen silane compound of formula (4) per mole of the double bond-bearing compound of formula (2) or (3).

The platinum catalyst used for the reaction includes chloroplatinic acid, an alcohol solution of chloroplatinic acid, a toluene or xylene solution of a platinum-1,3-divinyl-1,1,3,3-tetramethyldisiloxane complex, tetrakistriphenylphosphine platinum, dichlorobistriphenylphosphine platinum, dichlorobisacetonitrile platinum, dichlorobisbenzonitrile platinum, dichlorocyclooctadiene platinum or the like.

The amount of a platinum catalyst used is not critical. From the standpoint of reactivity and productivity, the amount is preferably within a range of 0.000001 to 0.01 mole, more preferably 0.00001 to 0.001 mole, per mole of the double bond-bearing compound of formula (2) or (3).

The reaction temperature is not critical and is generally within a range of 0 to 120° C., preferably from 20 to 100° C., and the reaction time ranges from 1 to 20 hours, preferably from 1 to 10 hours.

It will be noted that the reaction proceeds in a solvent-free condition although a solvent may be used. The solvent used for this purpose include a hydrocarbon solvent such as pentane, hexane, cyclohexane, heptane, isooctane, benzene, toluene, xylene or the like, an ether solvent such as diethyl ether, tetrahydrofuran, dioxane or the like, an ester solvent such as ethyl acetate, butyl acetate or the like, an aprotic polar solvent such as acetonitrile or N,N-dimethylformamide, and a chlorinated hydrocarbon solvent such as dichloromethane, chloroform or the like. These solvent may be used alone or in combination of two or more.

Among the compounds of the general formula (1) according to the invention, an organoxysilane compound (i.e. a compound of the formula wherein X is an organoxy group) can be prepared by converting a silane compound where X is a halogen atom into an organoxy group by means of an alcohol or a phenol.

EXAMPLE

The invention is described by way of examples, which should not be construed as limiting the invention thereto.

Example 1

Preparation of N,N',N'-tris(trimethylsilyl)-N-(2-aminoethyl)-3-aminopropyltriethoxysilane 31.7 g (0.1 mole) of N,N,N'-tris(trimethylsilyl)-N-allylethylenediamine and 0.07 g of a toluene solution of platinum-divinyltetramethyldisiloxane complex (with a platinum content of 3 wt %) were charged into a flask equipped with an agitator, a reflux condenser, a dropping funnel and a thermometer and heated to 50° C. After the inner temperature was kept constant, 16.4 g (0.1 mole) of trimethoxysilane was dropped for two hours, followed by agitation at the temperature for one hour. The resulting reaction solution was distilled to obtain 36.5 g of a fraction having a boiling point of 129 to 136° C./25 Pa.

Figure 1:
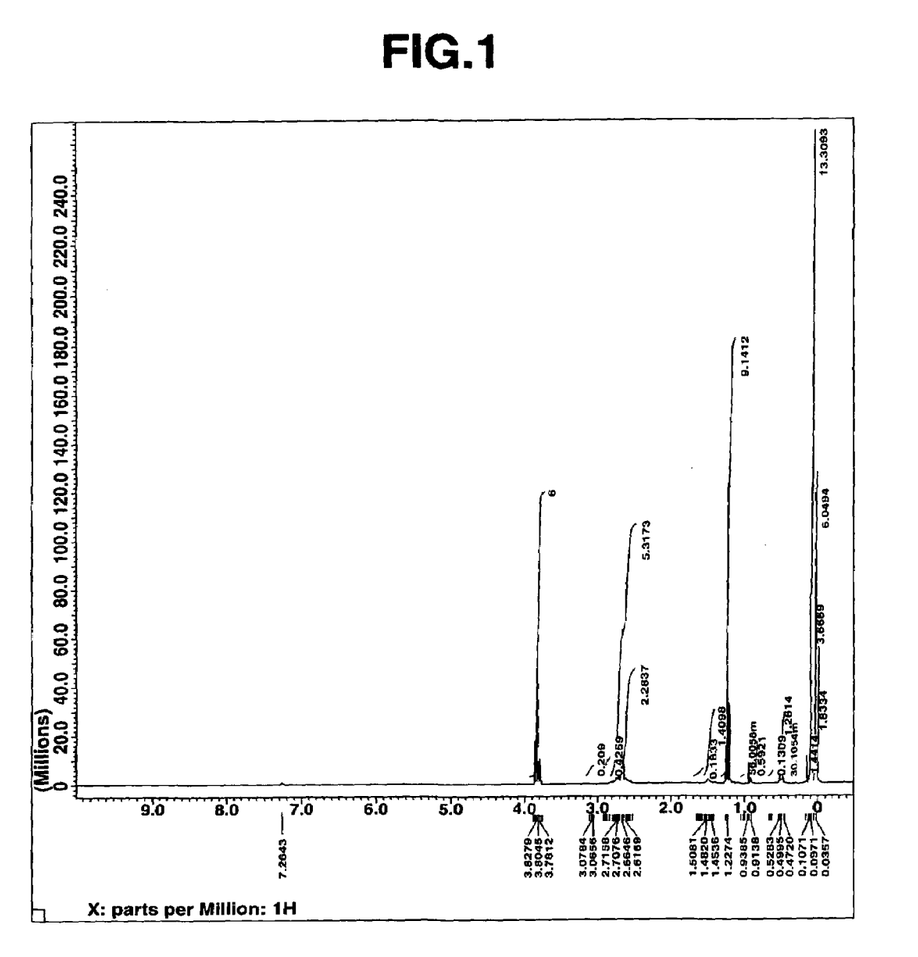
FIG. 1 is a $^1$H-NMR spectrum chart of a silane compound obtained in Example 1.
Figure 2:
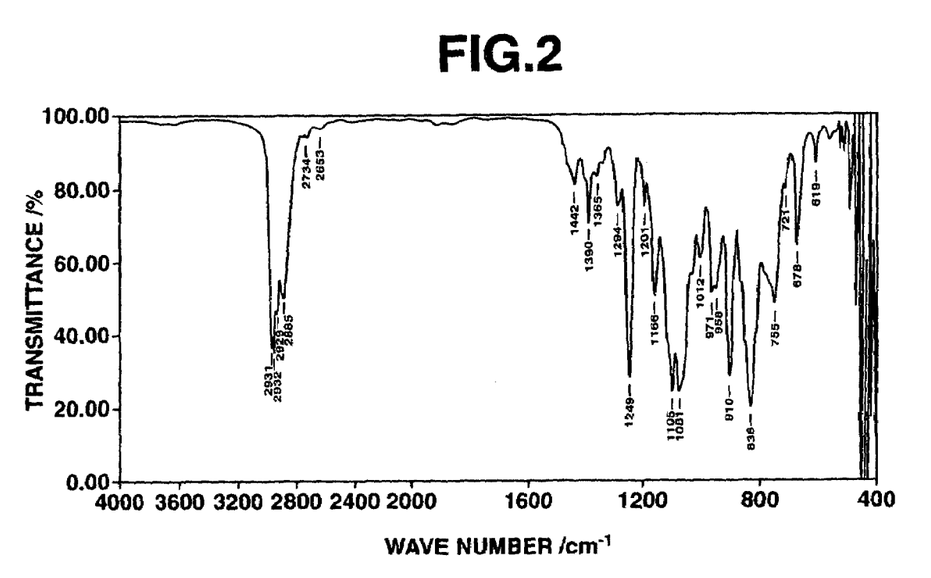
FIG. 2 is an IR spectrum chart of the silane compound obtained in Example 1.

The thus obtained fraction was subjected to measurements of mass spectrum, $^1$H-NMR spectrum (heavy chloroform solvent). The results of the mass spectrum are shown below. Moreover, the $^1$H-NMR spectrum chart and the IR spectrum chart are, respectively, shown in FIGS. 1 and 2.

Mass spectrum: m/z 465, 306, 188, 174, 163

These results reveal that the compound obtained was N,N',N'-tris(trimethylsilyl)-N-(2-aminoethyl)-3-aminopropyltriethoxysilane.

Example 2

Preparation of N,N',N'-tris(trimethylsilyl)-N-(2-aminoethyl)-3-aminopropylmethyldiethoxysilane 63.3 g (0.2 moles) of N,N,N'-tris(trimethylsilyl)-N-allylethylenediamine and 0.13 g of a toluene solution of platinum-divinyltetramethyldisiloxane complex (with a platinum content of 3 wt %) were charged into a flask equipped with an agitator, a reflux condenser, a dropping funnel and a thermometer and heated to 50° C. After the inner temperature was kept constant, 26.9 g (0.2 moles) of methyldiethoxysilane was dropped for two hours, followed by agitation at the temperature for one hour. The resulting reaction solution was distilled to obtain 63.4 g of a fraction having a boiling point of 117 to 124° C./20 Pa.

Figure 3:
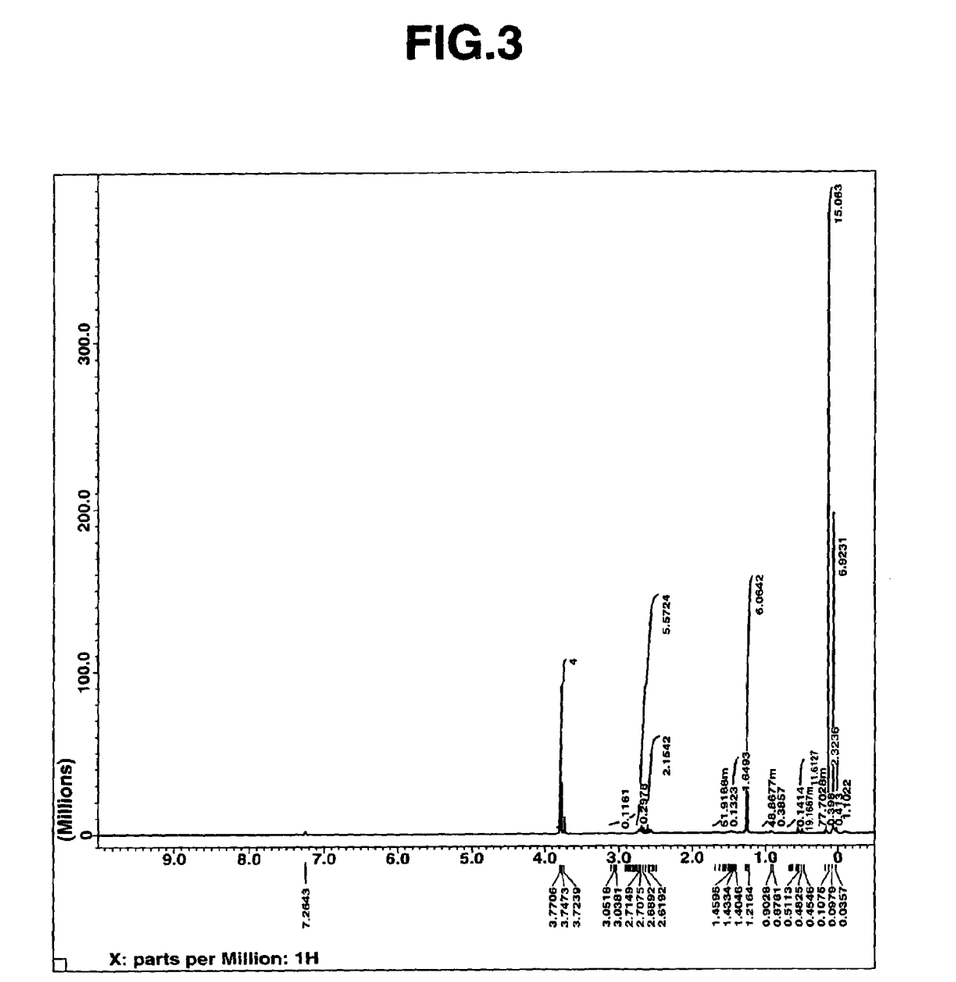
FIG. 3 is a $^1$H-NMR spectrum chart of a silane compound obtained in Example 2.
Figure 4:
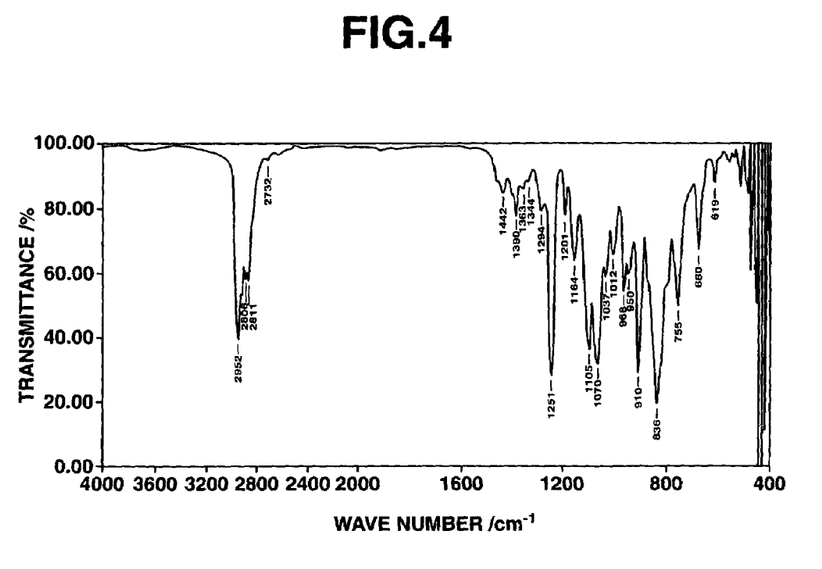
FIG. 4 is an IR spectrum chart of the silane compound obtained in Example 2.

The thus obtained fraction was subjected to measurements of mass spectrum, $^1$H-NMR spectrum (heavy chloroform solvent). The results of the mass spectrum are shown below. Moreover, the $^1$H-NMR spectrum chart and the IR spectrum chart are, respectively, shown in FIGS. 3 and 4.

Mass spectrum: m/z 435, 276, 188, 174, 133

These results reveal that the compound obtained was N,N',N'-tris(trimethylsilyl)-N-(2-aminoethyl)-3-aminopropylmethyldiethoxysilane.

Example 3

Preparation of 6,7-bis(trimethylsiloxy)-4-oxaheptyltriethoxysilane 83.0 g (0.3 moles) of glycereinebis(trimethylsilyl)-monoallyl ether and 0.20 g of a toluene solution of platinum-divinyltetramethyldisiloxane complex (with a platinum content of 3 wt %) were charged into a flask equipped with an agitator, a reflux condenser, a dropping funnel and a thermometer and heated to 50° C. After the inner temperature was kept constant, 49.3 g (0.3 moles) of triethoxysilane was dropped for two hours, followed by agitation at the temperature for one hour. The resulting reaction solution was distilled to obtain 83.9 g of a fraction having a boiling point of 113 to 117° C./27 Pa.

Figure 5:
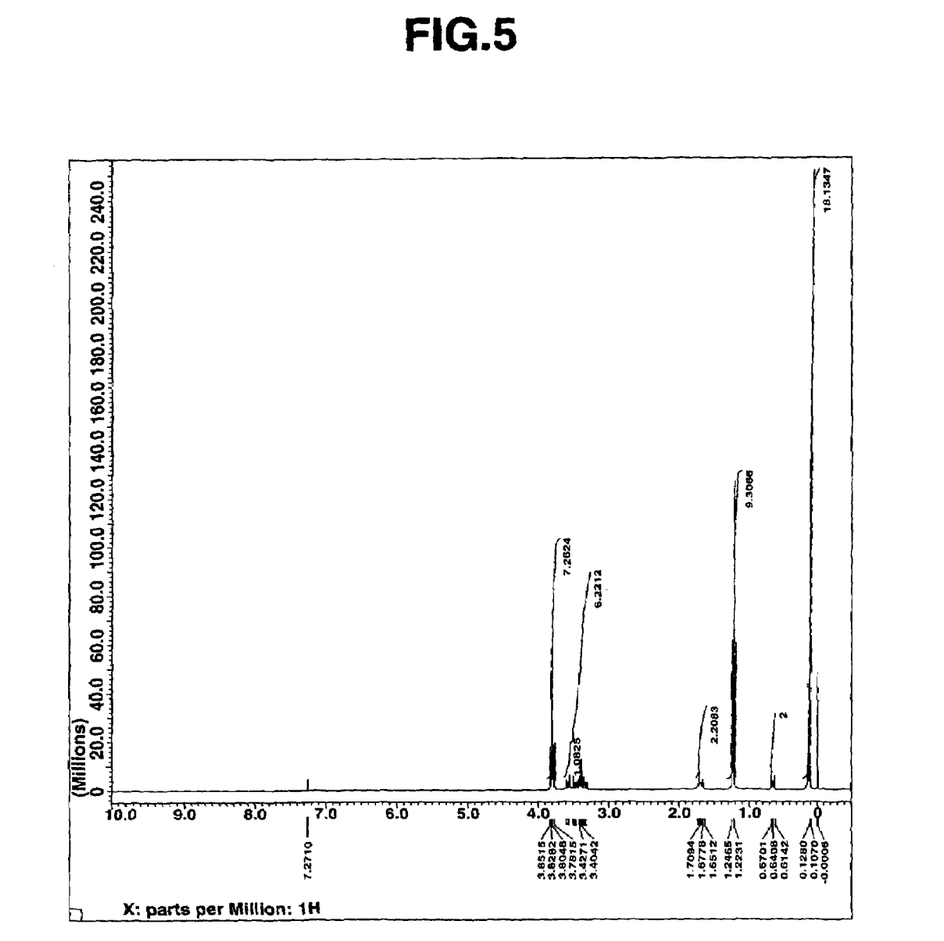
FIG. 5 is a $^1$H-NMR spectrum chart of a silane compound obtained in Example 3.
Figure 6:
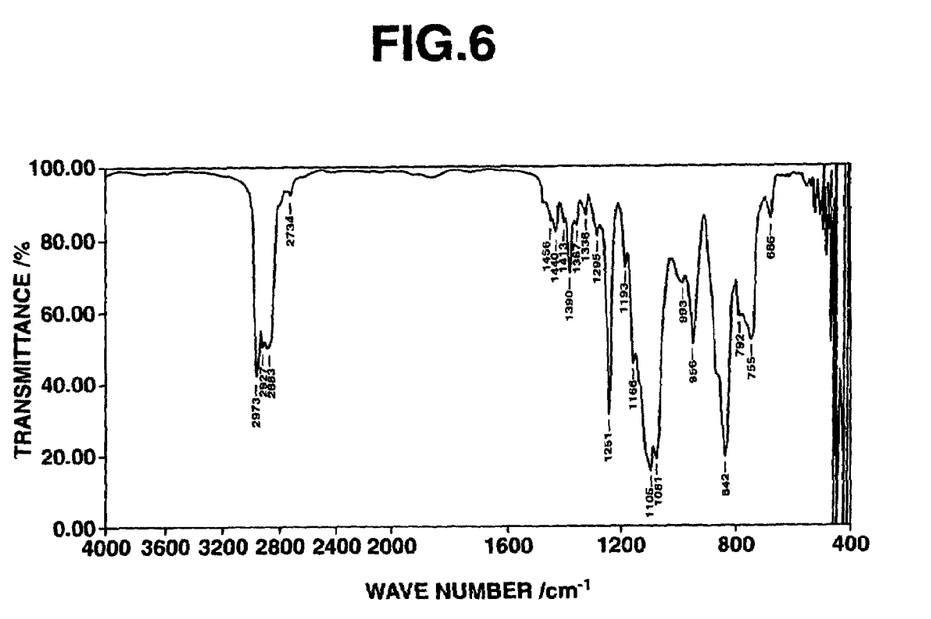
FIG. 6 is an IR spectrum chart of the silane compound obtained in Example 3.

The thus obtained fraction was subjected to measurements of mass spectrum, $^1$H-NMR spectrum (heavy chloroform solvent). The results of the mass spectrum are shown below. Moreover, the $^1$H-NMR spectrum chart and the IR spectrum chart are, respectively, shown in FIGS. 5 and 6.

Mass spectrum: m/z 425, 291, 205, 163, 73

These results reveal that the compound obtained was 6,7-bis(trimethylsiloxy)-4-oxaheptyltriethoxysilane.

Example 4

Preparation of 6,7-bis(trimethylsiloxy)-4-oxaheptylmethyldiethoxysilane 83.0 g (0.3 moles) of glycereinebis(trimethylsilyl)-monoallyl ether and 0.20 g of a toluene solution of platinum-divinyltetramethyldisiloxane complex (with a platinum content of 3 wt %) were charged into a flask equipped with an agitator, a reflux condenser, a dropping funnel and a thermometer and heated to 50° C. After the inner temperature was kept constant, 40.3 g (0.3 moles) of methyldiethoxysilane was dropped for two hours, followed by agitation at the temperature for one hour. The resulting reaction solution was distilled to obtain 85.1 g of a fraction having a boiling point of 101 to 103° C./15 Pa.

Figure 7:
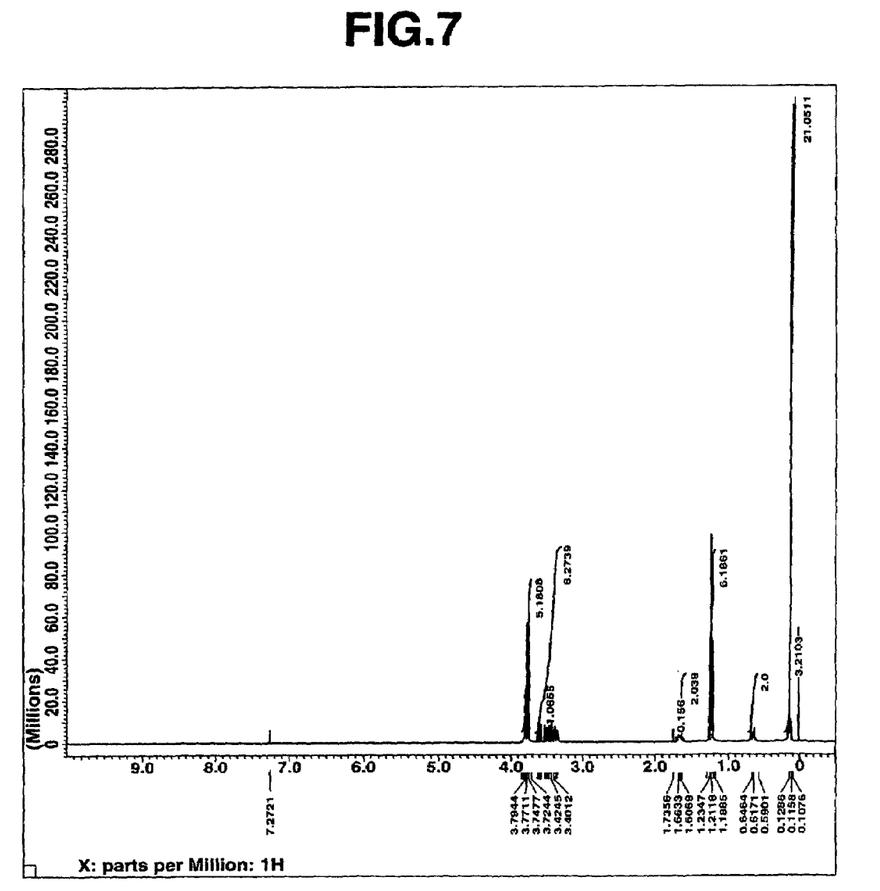
FIG. 7 is a $^1$H-NMR spectrum chart of a silane compound obtained in Example 4.
Figure 8:
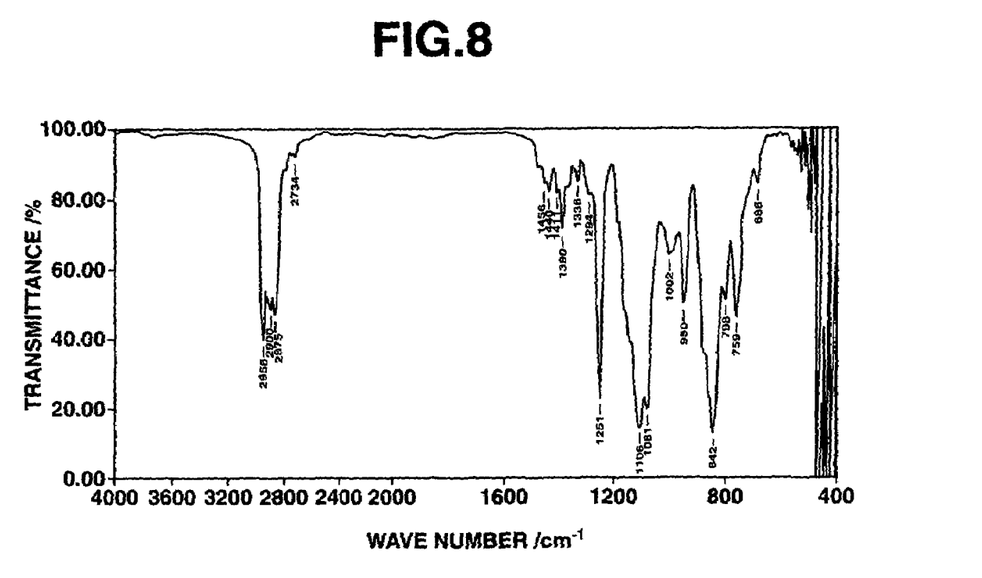
FIG. 8 is an IR spectrum chart of the silane compound obtained in Example 4.

The thus obtained fraction was subjected to measurements of mass spectrum, $^1$H-NMR spectrum (heavy chloroform solvent). The results of the mass spectrum are shown below. Moreover, the $^1$H-NMR spectrum chart and the IR spectrum chart are, respectively, shown in FIGS. 7 and 8.

Mass spectrum: m/z 395, 261, 205, 133, 73

These results reveal that the compound obtained was 6,7-bis(trimethylsiloxy)-4-oxaheptylmethyldiethoxysilane.

Japanese Patent Application No. 2004-119293 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silane compound of the following formula (1) having two or more protected functional groups wherein A represents a group of the following formula wherein $R^1$, $R^2$ and $R^3$ each independently represent a monovalent hydrocarbon group having 1 to 10 carbon atoms, a is an integer of 1 to 10, and b is an integer of 1 to 10, or a group of the following formula wherein $R^1$, $R^2$ and $R^3$ are as defined above, R represents a linear or branched, divalent hydrocarbon group having 2 to 10 carbon atoms, X represents an organoxy group having 1 to 10 carbon atoms, and n is 0,1 or 2.

2. The silane compound of claim 1 wherein $R^1$, $R^2$ and $R^3$ each independently have 1 to 6 carbon atoms.

3. The silane compound of claim 1 wherein $R^1$, $R^2$ and $R^3$ are each independently selected from the group consisting of a methyl group, an ethyl group, a propyl group, an isopropyl group, a butyl group, an isobutyl group, a tert-butyl group, a pentyl group, a cyclopentyl group, a hexyl group, a cyclohexyl group, a heptyl group, an octyl group, a decyl group, a vinyl group, an allyl group, a propenyl group, and a phenyl group.

4. The silane compound of claim 1 wherein R has 3 to 10 carbon atoms.

5. The silane compound of claim 1 wherein R is selected from the group consisting of an alkylene group, and an aralkylene group.

6. The silane compound of claim 1 wherein R is selected from the group consisting of a trimethylene group, a tetramethyl group, a hexamethylene group, and an isobutylene group.

7. The silane compound of claim 1 wherein the organoxy group has 1 to 6 carbon atoms.

8. The silane compound of claim 1 wherein the organoxy group is selected from the group consisting of a methoxy group, an ethoxy group, a propoxy group, an n-butoxy group, an isobutoxy group, a tert-butoxy group, an acyloxy group, an acetoxy group, an acryloxy group, a methacryloxy group, and a phenoxy group.

9. The silane compound of claim 1 which is N,N',N'-tris(trimethylsilyl)-N-(2-aminoethyl)-3-aminopropyltriethoxysilane.

10. The silane compound of claim 1 which is N,N',N'-tris(trimethylsilyl)-N-(2-aminoethyl)-3-aminopropylmethyldiethoxysilane.

11. The silane compound of claim 1 which is 6,7-bis(trimethylsiloxy)-4-oxaheptyltriethoxysilane.

12. A method for preparing the silane compound of formula (1) having two or more protected functional groups $$A-R-Si(CH_3)_{n-1}X_{3-n} \quad (1)$$

wherein A represents a group of the following formula wherein $R^1$, $R^2$ and $R^3$ each independently represent a monovalent hydrocarbon group having 1 to 10 carbon atoms, a is an integer of 1 to 10, and b is an integer of 1 to 10, or a group of the following formula wherein $R^1$, $R^2$ and $R^3$ are as defined above, R represents a linear or branched, divalent hydrocarbon group having 2 to 10 carbon atoms, X represents an organoxy group having 1 to 10 carbon atoms, and n is 0, 1 or 2 which comprises reacting, in the presence of a platinum catalyst, a compound of the following general formula (2) or (3) having a double bond $$A-R'-CH=CH_2 \quad (2)$$

$$A-CH=CH_2 \quad (3)$$

wherein A is as defined above, and R' represents a linear or branched divalent hydrocarbon group having 1 to 8 carbon atoms, and a hydrogen silane compound of the following general formula (4)

$$HSi(CH_3)_n X_{3-n} \quad (4)$$

wherein X and n are as defined above.

13. The method of claim 12 wherein the platinum catalyst is selected from the group consisting of: chloroplatinic acid; a complex of platinum-13-divinyl-1,1,3,3-tetramethyldisiloxane; tetrakistriphenylphosphine platinum; dichlorobistriphenylphosphine platinum; dichlorobisacetonitrile platinum; dichlorobisbenzonitrile platinum; and dichlorocyclooctadiene platinum.

14. The method of claim 12 wherein the reacting occurs at a temperature within the range of 0 to 120° C.

15. The method of claim 12 wherein the reacting occurs at a temperature within the range of 20 to 100° C.

* * * * *